(12) United States Patent
Faure

(10) Patent No.: US 6,375,656 B1
(45) Date of Patent: Apr. 23, 2002

(54) DEVICE FOR FIXING A ROD TO A THIN BONE WALL

(75) Inventor: Alexis Faure, Nantes (FR)

(73) Assignee: DIMSO (Distribution Medicale du Sud-Ouest) (FR)

( * ) Notice: Subject to any disclaimer, the term of this patent is extended or adjusted under 35 U.S.C. 154(b) by 0 days.

(21) Appl. No.: 09/529,450

(22) PCT Filed: Oct. 12, 1998

(86) PCT No.: PCT/FR98/02178

§ 371 Date: Jun. 13, 2000

§ 102(e) Date: Jun. 13, 2000

(87) PCT Pub. No.: WO99/18877

PCT Pub. Date: Apr. 22, 1999

(30) Foreign Application Priority Data

Oct. 13, 1997 (FR) .......................................... 97 12776

(51) Int. Cl.[7] .................................................. A61B 17/70
(52) U.S. Cl. ........................................... 606/72; 606/61
(58) Field of Search ............................... 606/53, 54, 60, 606/61, 72

(56) References Cited

U.S. PATENT DOCUMENTS

| | | | |
|---|---|---|---|
| 4,369,770 A | * | 1/1983 | Bacal et al. |
| 4,815,453 A | * | 3/1989 | Cotrel |
| 5,005,562 A | * | 4/1991 | Cotrel |
| 5,010,879 A | * | 4/1991 | Moriya et al. |
| 5,067,955 A | * | 11/1991 | Cotrel .......................... 606/61 |
| 5,403,314 A | | 4/1995 | Currier ......................... 606/61 |
| 5,496,321 A | * | 3/1996 | Puno et al. .................... 606/61 |

FOREIGN PATENT DOCUMENTS

| | | |
|---|---|---|
| EP | 0 248 103 | 12/1987 |
| WO | WO 95 22291 | 8/1995 |

\* cited by examiner

*Primary Examiner*—David O. Reip
(74) *Attorney, Agent, or Firm*—Lerner, David, Littenberg, Krumholz & Mentlik, LLP

(57) ABSTRACT

The invention concerns an implantable device for fixing a rod in a rather thin bone wall comprising two parts each comprising a body with a passage for receiving the rod, and a curved hook extending laterally relative to the body. Each hook is shaped such that the two hooks facing each other can be simultaneously inserted, by mutually tilting the two parts urging their bodies closer to each other, in an opening arranged in the wall, and be mutually spaced rearwards as said bodies are brought closer to each other. The rod received in said passages of the two bodies is capable of preventing any reverse tilting of said parts. The invention is particularly useful for fixing a rod for backbone osteosynthesis in the flat part of the skull occipital bone.

18 Claims, 1 Drawing Sheet

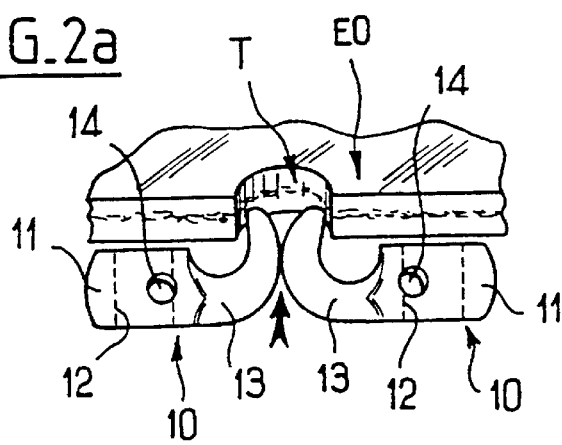
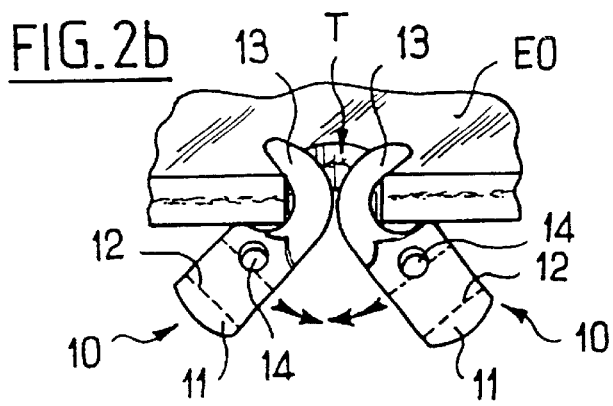
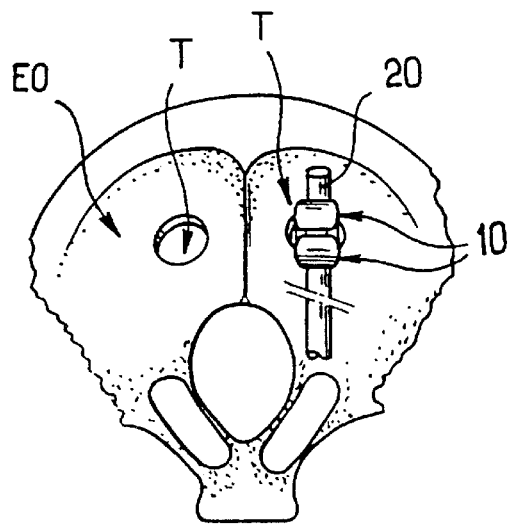
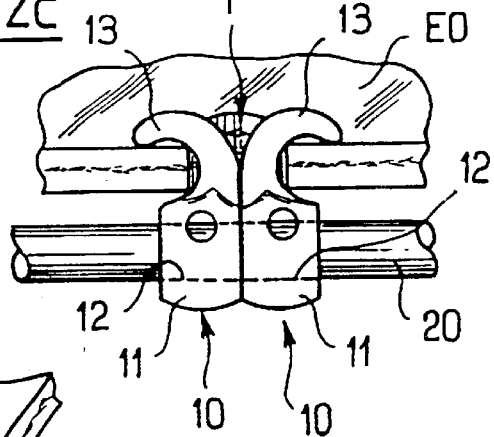
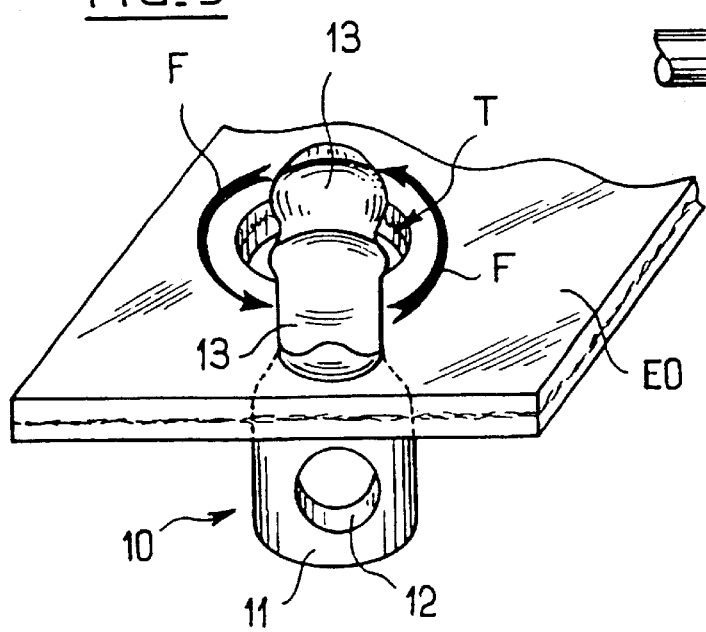

DEVICE FOR FIXING A ROD TO A THIN BONE WALL

BACKGROUND OF THE INVENTION

1. Field of the Invention

The present invention relates in general to an implantable device for occipital fixing, and in particular to a device designed to fix a patient's occipital bone to the end of a system for osteosynthesis of the spine and having longitudinal rods.

2. Description of the Prior Art

Rod systems for osteosynthesis of the spine are well known. They comprise two rods that are generally cylindrical and that are secured to respective sides of the vertebrae by means of screws and/or hooks.

Although such fixings are entirely suitable for securing the vertebrae, it is necessary to design special fixings when such a system needs to be extended to the skull, and more precisely to the occipital bone.

The present invention seeks to propose a device for anchoring in a bone wall of relatively small thickness and suitable for use in fixing rods of an osteosynthesis system for the spinal column to the occipital bone, which device provides satisfactory mechanical strength, while being simple to make and implement, and [minimizing] the need for holes to be made through said bone wall.

SUMMARY OF THE INVENTION

Thus, the present invention provides an implantable device for fixing a rod to a thin bone wall, in particular for fixing a rod of a system for osteosynthesis of the spine to the wall of the occipital bone of the skull, the device being characterized in that it comprises two parts each comprising both a body in which there is formed a passage for receiving the rod, and also a curved hook extending laterally relative to the body, in that each hook is of a shape such that the two hooks when placed face to face can be inserted simultaneously into an opening formed in said bone wall, the hooks being inserted by tilting the two parts in opposite directions so as to tend to move their bodies towards each other, the hooks moving away from each other behind said wall as said bodies move towards each other, and in that said passages of the two bodies come into alignment once the bodies have come close together, and the rod received therein is suitable for preventing said parts from tilting in the opposite direction.

Preferred but non-limiting features of the device of the invention are as follows:

- the body of each part is generally oval in shape with at least one plane face, and said bodies are suitable for being placed essentially in contact with each other via their facing plane faces so as to ensure that both passages are in axial alignment;
- each hook has a root region extending from the vicinity of said plane face, essentially at right angles relative to the axis of the passage, and an end portion extending substantially parallel to the axis of the passage;
- the overall size of each hook as measured in a direction parallel to the axis of the corresponding passage is greater than the thickness of the body in said direction;
- the body has a second plane face substantially parallel to the first plane face;
- each hook is of a thickness that tapers progressively away from its root portion towards its free end;
- each hook is of a width that is substantially constant over its entire extent;
- each part includes means for locking the rod in its passage;
- the locking means comprise a screw engaged in tapping formed in the body and opening out into the passage; and
- the two parts are identical.

BRIEF DESCRIPTION OF THE DRAWINGS

Other aspects, objects, and advantages of the present invention will appear more clearly on reading the following description of a presently preferred embodiment of the invention given by way of example and described with reference to the accompanying drawing, in which:

FIG. 1 is a view of the occipital bone of a patient seen from outside the skull;

FIGS. 2a to 2c are side views in perspective of two anchor elements of an occipital fixing device of the invention during three successive stages of the process of installing them; and FIG. 3 is a perspective view of the device of the invention seen from inside the posterior cranial fossa defined by the occipital bone.

DESCRIPTION OF THE PREFERRED EMBODIMENTS

With reference initially to FIG. 1, there is shown the region of the—occipital-bone EO of a patient.

Using a trepan, the surgeon has made two generally circular holes therein referenced T, which holes are of determined diameter and are spaced apart laterally by a determined distance.

With reference now to FIGS. 2a to 2c and 3, a fixing device of the invention comprises two identical parts 10, 10. Each part comprises a generally oval-shaped body 11 having generally plane opposite faces with a through cylindrical bore 12 of well determined diameter made therethrough.

The body is extended laterally by a hook-forming portion 13 having a root portion that extends substantially at right angles relative to the axis of the bore 12 close to one of the plane faces of the body 11, said root portion being extended in curved manner so as to terminate substantially parallel to said axis, beyond the other plane face of the body.

Advantageously, the width of the hook 13 is essentially constant, and slightly smaller than the outside diameter of the body 11, and it tapers progressively towards its free end.

As can be seen in particular in FIG. 3, the hook 13 has a free end that is slightly rounded.

The device comprising two parts 10, 10 is put into place as described below with reference to FIGS. 2a to 2c.

In FIG. 2a, it can be seen that the two parts 10, 10 are positioned facing each other in such a manner that the end regions of the hooks 13 are adjacent and point into the hole T, penetrating a little therein. This can be achieved by giving overall dimensions to the hooks 13 as measured parallel to the axes of the respective bores 12 that are greater than the thickness of the body 11 between its two opposite plane faces.

It will be observed at this point that the diameter of the hole T is selected in such a manner that in this position the ends of the hooks 13 can be engaged side by side in the hole T by appropriately tilting the two parts 10, 10 in opposite directions. An intermediate stage in this tilting is shown in FIG. 2b, where it can be seen that the hooks have begun to engage in the posterior cranial fossa, moving laterally away from each other so that the distance between the free ends thereof becomes greater than the diameter of the hole T.

This tilting movement is continued until the bodies 11 of the two parts 10, 10 are side by side and their hook-forming portions 13 are in a hooking relationship with the wall of the occipital bone. It will be understood that to achieve this hooking, the overall length of each hook 13 as measured in a direction parallel to the axis of the bore 12, must be greater than the radius of the hole T formed through the occipital bone.

At this stage, it will be observed that the device constituted by the two parts occupying the position shown in FIG. 2c (prior to insertion of the rod 20 as described below) can pivot freely about an axis that coincides essentially with the axis of the hole T, as represented by arrows F in FIG. 3.

It will also be observed that in this position, the bores 12 of the two parts 10 are in general alignment. As a result, a rod 20 constituting a rod of a system for osteosynthesis of the spine can be inserted into both bores, as shown in FIG. 2c.

Once the rod has been inserted, the parts 10, 10 are prevented from tilting in the opposite direction by said rod 20, 50 the device is locked in the wall of the occipital bone.

In addition, if it is desired to obtain firm locking between the rod 20 and the two parts 10, 10, it is possible to fit each of the parts 10 with any appropriate clamping means for this purpose.

In the embodiment shown, the clamping means comprise a tapped orifice 14 formed in the body 11 of each part 10 between the outside wall of said body and the bore 12.

A clamping screw (not shown but conventional), e.g. fitted with a hollow hexagonal socket for tightening purposes, can be screwed into the orifice 14 after the rod 20 has been inserted and once it occupies the desired position, thereby exerting pressure on said rod so as to lock it in the corresponding housing.

Entirely reliable hooking is thus achieved by means of a device that is extremely simple, being constituted by two identical parts, and by forming a simple circular hole in the occipital case by means of a trepan.

In addition, it will be understood from the above, that the device can be put into place easily and quickly by a surgeon.

Naturally, the two parts 10, 10 and the clamping screws are made of biocompatible alloy such as a titanium alloy or a stainless steel alloy.

Naturally, the present invention is not limited in any way to the embodiment described and shown, and the person skilled in the art will know how to apply any variant or modification thereof within the spirit of the invention.

In particular, although the description above relates to the rod 20 being received in through bores formed in the bodies of the parts 10, the invention also applies to the case where the rod is fixed to each part by other means, and in particular when it is placed in an open channel and is locked therein by an element that closes the channel, in particular a screw element.

What is claimed is:

1. A method for implanting a device for a fixing rod to a thin bone wall, in particular for fixing a rod of a system for osteosynthesis of the spine to the wall of the occipital bone of the skull, the device comprising a rod and two parts each comprising both a body in which there is formed a passage for receiving the rod, and also a curved hook extending laterally relatively to the body, the method comprising:

placing the two hooks face to face;

inserting the hooks simultaneously into a first opening formed in said bone wall, the hooks being inserted by tilting the two parts in opposite directions so as to tend to move their bodies towards each other, the hooks moving away from each other behind said wall as said bodies move towards each other;

aligning said passages of the two bodies once the bodies have come together with the parts in mutual contact; and receiving the rod therein, thereby preventing said parts from tilting in the opposite direction.

2. The method as set forth in claim 1 further comprising forming a second opening in said bone wall spaced from said first opening and inserting a second pair of hooks in said second opening.

3. The method as set forth in claim 2 further comprising inserting a second rod in the rod receiving passage of said second pair of hooks.

4. The method as set forth in claim 1 wherein said first opening is circular and has a radius which is less than an overall length of the hook portion of one of said hooks.

5. The method as set forth in claim 1 wherein said tilting of said pair of hook bodies towards one another is continued until planar outer surfaces of said bodies are in side by side relationship.

6. The method as set forth in claim 5 further including rotating said hooks about the circumference of said first opening.

7. The method as set forth in claim 1 further including the step of locking the rod in a fixed position with respect to the hook bodies.

8. The method as set forth in claim 7 wherein said locking of the rod is accomplished by inserting a set screw through a hook body intersecting the rod receiving passage.

9. The method as set forth in claim 1 wherein the hook portions are placed in contact over said first opening and the hook bodies are rotated about 90° towards one another.

10. A method for attaching a rod to a bone wall comprising;

forming a first opening in the bone wall;

placing a pair of hooks over said first opening, said hooks each having a body in which a rod receiving passage extending along an axis is formed and a curved hook portion extending from said body, said hooks placed over said opening with said hook portions facing said bone opening;

rotating said pair of hook bodies towards one another so that said hook portions engage a periphery of said opening in the bone wall;

aligning said axis of said rod receiving passages in a coaxial manner; and inserting a rod through said coaxially aligned passages to prevent said hook bodies from rotating away from each other.

11. The method as set forth in claim 10 further comprising forming a second opening in said bone wall spaced from said first opening and inserting a second pair of hooks in said second opening.

12. The method as set forth in claim 11 further comprising inserting a second rod in the rod receiving passage of said second pair of hooks.

13. The method as set forth in claim 10 wherein said first opening is circular and has a radius which is less than an overall length of the hook portion of one of said hooks.

14. The method as set forth in claim 10 wherein said rotating of said pair of hook bodies towards one another is continued until planar outer surfaces of said bodies are in side by side relationship.

15. The method as set forth in claim 14 further including rotating said hooks about the circumference of said first opening.

16. The method as set forth in claim 10 further including the step of locking the rod in a fixed position with respect to the hook bodies.

17. The method as set forth in claim 16 wherein said locking of the rod is accomplished by inserting a set screw through a hole in a hook body intersecting the rod receiving passage.

18. The method as set forth in claim 10 wherein the hook portions are placed in contact over said first opening and the hook bodies are rotated about 90° towards one another.

* * * * *

UNITED STATES PATENT AND TRADEMARK OFFICE
CERTIFICATE OF CORRECTION

PATENT NO. : 6,375,656 B1
DATED : April 23, 2002
INVENTOR(S) : Alexis Faure

It is certified that error appears in the above-identified patent and that said Letters Patent is hereby corrected as shown below:

Column 1,
Line 6, change "1. Field of the Invention".
Line 12, cancel "2. Description of the Prior Art".

Column 3,
Line 66, cancel "a" (third occurrence).
Line 66, after "fixing" insert -- a --.

Signed and Sealed this

Fifteenth Day of October, 2002

Attest:

JAMES E. ROGAN
Attesting Officer
Director of the United States Patent and Trademark Office